(12) United States Patent
Lee et al.

(10) Patent No.: US 8,262,284 B2
(45) Date of Patent: Sep. 11, 2012

(54) SIMULATION TEST SYSTEM FOR THERMAL IMPACT AGEING OF POWER TRANSMISSION INSULATOR

(75) Inventors: Won-Kyo Lee, Daejeon (KR); In-Hyuk Choi, Daejeon (KR); Jong-Kee Choi, Daejeon (KR); Kap-Cheol Hwang, Daejeon (KR)

(73) Assignee: Korea Electric Power Corporation, Gangnam-Gu (KR)

( * ) Notice: Subject to any disclaimer, the term of this patent is extended or adjusted under 35 U.S.C. 154(b) by 566 days.

(21) Appl. No.: 12/566,910

(22) Filed: Sep. 25, 2009

(65) Prior Publication Data

US 2010/0080261 A1 Apr. 1, 2010

(30) Foreign Application Priority Data

Sep. 29, 2008 (KR) ........................ 10-2008-0095100

(51) Int. Cl.
*G01N 3/60* (2006.01)
(52) U.S. Cl. .................................. 374/57; 374/45; 374/5
(58) Field of Classification Search ................... 374/57, 374/45, 5, 137; 73/865.6
See application file for complete search history.

(56) References Cited

U.S. PATENT DOCUMENTS

| | | | | |
|---|---|---|---|---|
| 3,983,742 | A * | 10/1976 | Suga | 374/57 |
| 5,098,196 | A * | 3/1992 | O'Neill | 374/11 |
| 5,601,364 | A * | 2/1997 | Ume | 374/57 |
| 5,769,540 | A * | 6/1998 | Schietinger et al. | 374/127 |
| 6,146,013 | A * | 11/2000 | Huetter et al. | 374/46 |
| 6,877,894 | B2 * | 4/2005 | Vona et al. | 374/45 |
| 7,013,742 | B2 * | 3/2006 | Beraud | 73/865.6 |
| 7,318,672 | B2 * | 1/2008 | Hardcastle, III | 374/109 |

(Continued)

FOREIGN PATENT DOCUMENTS

| | | |
|---|---|---|
| KR | 10-2000-0015474 A | 3/2000 |
| KR | 20080073084 A | 8/2008 |
| KR | 10-2009-0055391 A | 6/2009 |

OTHER PUBLICATIONS

Kim, et al. (2008). A study on voltage and reactive power control methodology using integer programming and local subsystems. *Integer Programming*, 57(4), 543-550.

(Continued)

*Primary Examiner* — Yaritza Guadalupe-McCall
(74) *Attorney, Agent, or Firm* — McDermott Will & Emery LLP

(57) ABSTRACT

The present invention relates to a simulation test system for thermal impact ageing of a power transmission insulator which simulation tests an influence of a forest fire on the power transmission insulator. The present invention provides a simulation test system of thermal impact ageing for a power transmission insulator, which includes a heating chamber provided with a flame supplying part and electric heating parts in fireproof walls and a partition wall having an opening/closing door in a lower part thereof; a cooling chamber placed under the heating chamber and provided with a cooling nozzle in a fireproof wall; a sample lifting device for selectively lifting a test sample up and down through the heating chamber and the cooling chamber; a door transporting device for slidingly moving the opening/closing door; and a central control part for controlling the flame supplying part, the electric heating part, the opening/closing door, the cooling nozzle, the sample lifting device and the door transporting device independently and respectively. Therefore, since the heating chamber and the cooling chamber are configured independently from each other, heating and cooling tests for the test sample can be performed individually or together.

12 Claims, 4 Drawing Sheets

U.S. PATENT DOCUMENTS

| | | | |
|---|---|---|---|
| 7,329,043 B2* | 2/2008 | Ogle et al. | 374/112 |
| 7,371,006 B2* | 5/2008 | Schick | 374/10 |
| 7,448,796 B2* | 11/2008 | Schick | 374/31 |
| 7,677,795 B2* | 3/2010 | Schick | 374/10 |
| 7,815,366 B2* | 10/2010 | Okamura et al. | 374/45 |
| 7,862,231 B2* | 1/2011 | Liu | 374/141 |
| 7,883,266 B2* | 2/2011 | Campbell et al. | 374/5 |
| 2008/0049810 A1* | 2/2008 | Schick | 374/31 |
| 2009/0034579 A1* | 2/2009 | Schick | 374/10 |
| 2010/0080261 A1* | 4/2010 | Lee et al. | 374/57 |
| 2012/0008925 A1* | 1/2012 | Yoshimoto et al. | 374/121 |

OTHER PUBLICATIONS

Min, et al. (2006). Reliability assessment of forest fire on ehv plymer insulator strings. *Pr Inst Electr Eng*, 2006(7), 436-437.

Korean Office Action issued in Korea Patent Application No. 10-2008-0106744, dated Jul. 30, 2010.

Korean Office Action issued in Korea Patent Application No. 10-2008-0095100, dated May 14, 2010.

* cited by examiner

AIR COOING/INFUSION WATER COOLING

SIMULATION TEST SYSTEM FOR THERMAL IMPACT AGEING OF POWER TRANSMISSION INSULATOR

This is an application claiming foreign priority benefits under 35 U.S.C. 119 of Korean Application No. 10-2008-0095100, filed on Sep. 29, 2008, the entire content of which is hereby incorporated by reference in its entirety.

BACKGROUND OF THE INVENTION

1. Field of the Invention

The present invention relates to a simulation test system for thermal impact ageing of a power transmission insulator, and more particularly, to a simulation test system for thermal impact ageing of a power transmission insulator which simulation tests an influence of a forest fire on the power transmission insulator.

2. Description of Related Art

In general, a power transmission facility such as a high voltage electric wire is installed in a mountain area in which there is almost no visitor and it is therefore difficult to extinguish a forest fire quickly when the forest fire is generated around power transmission facility and heat and flame due to the forest fire cause great damage to the power transmission facility.

Although this damage of the power transmission facility by the forest fire is a cause of lowering in reliability of a power transmission system due to breakdown and interruption of power transmission lines, detailed studies on the damage of the power transmission facility by the forest fire is currently in poor condition. Also, since data for studies on an influence of the forest fire on the power transmission facility in a domestic forest environment are insufficient, various studies for finding out the cause of the breakdown including flashover and disconnection and preparing measures for the system operation when the forest fire is generated are required. Further, studies for deterioration properties and replacement standard of main power transmission facility after generation of the forest fire is also insufficient and it is urgent to prepare measures therefor.

Meanwhile, when the power transmission insulator is affected by the flame of the forest fire, interfacial stresses due to thermal impact are a main cause of deterioration and breakdown since the insulator is compositely constituted of different materials including porcelain, cement, bronze, and enamel.

Result of analyzing a flame temperature and properties of the forest fire based on that the power transmission insulator is exposed to the forest fire in the domestic forest condition (height, fuel condition) shows probability of being exposed to a temperature in a range of 200 to 800° C. if a clearance between the insulator and the earth is 2 to 6 meter when considering kinds of the domestic woods and height of the power transmission tower. Also, the result show that a rising time to the maximum flame temperature is about 60 seconds, a falling time is about 300 seconds and a retention time of the flame temperature is 60 to 200 seconds.

From FIG. 1, it can be found that a temperature distribution according to flame of the forest fire is, taken as a whole, from 100 to 300° C. From FIG. 1, it can also be found that the insulator can be exposed to heat at 800° C. or more for tens minutes or more in a large scale forest fire when radiant heat is activated.

Although this experimental result is an important factor for analyzing deterioration of the power transmission insulator by the thermal impact according to exposure to the forest fire, building and technical studies for an accelerated deterioration analyzing system based on such data is so far insufficient.

In a currently available thermal impact ageing test system, the test is implemented with varying a temperature from −60° C. to maximum 700° C. by applying heat in an electric heating manner. However, the conventional thermal impact ageing test system has a limitation in that it is difficult to control the maximum temperature of the flame of the forest fire (about 800° C.), and a temperature inducing thermal impact deterioration (about 300° C.), and thus there is a need for a simulation test system for controlling the maximum temperature of the flame of the forest fire sufficiently.

SUMMARY OF THE INVENTION

Embodiments of the present invention are directed to a simulation test system for thermal impact ageing of a power transmission insulator which allows deterioration test according to the thermal impact ageing of the power transmission insulator at the maximum temperature of flame of a forest fire.

To achieve the object of the present invention, the present invention provides a simulation test system of thermal impact ageing for a power transmission insulator, which includes a heating chamber provided with a flame supplying part in a side of fireproof wall and electric heating parts in two sides of the fireproof walls in a longitudinal direction of the fireproof walls; a sample lifting device for selectively lifting a test sample up and down in the heating chamber; and a central control part for controlling the flame supplying part, the electric heating part and the sample lifting device independently and respectively.

Preferably, the simulation test system further includes a cooling chamber formed independently under the heating chamber. Preferably, the cooling chamber is provided with cooling nozzles for spraying cooling water on the fireproof walls in two sides thereof to cool the test sample.

Preferably, a partition wall provided with an opening is formed between the heating chamber and the cooling chamber, and an opening/closing door for selectively passing the test sample through the opening is provided in the opening of the partition wall.

Preferably, the opening/closing door slidingly moves with respect to one side of the partition wall by a door transporting device to open and close the opening. Preferably, the door transporting device includes a fixation rack which is fixed to one side of the opening/closing door and is formed with a gear part along its surface and a door operating motor having, at its shaft, a pinion gear which is engaged with the gear part of the fixation rack.

Preferably, the sample lifting device includes a support rack which supports the test sample and is formed with a gear part along its surface and a sample transporting motor having, at its shaft, a pinion gear which is engaged with the gear part of the support rack.

Preferably, the heating chamber is provided with a ventilator for exhausting smoke generated by the flame supplying part.

Preferably, the central control part controls a temperature of the flame supplying part and a temperature of the electric heating part in the heating chamber and a distance between the flame supplying part and the test sample through the sample lifting device. Also, preferably, the central control part controls amount and time of cooling water spray from the cooling nozzle in the cooling chamber.

Further, the present invention provides a simulation test system of thermal impact ageing for a power transmission insulator, which includes a heating chamber provided with a flame supplying part and electric heating parts in fireproof walls and a partition wall having an opening/closing door in a lower part thereof; a cooling chamber placed under the heating chamber and provided with a cooling nozzle in a fireproof wall; a sample lifting device for selectively lifting a test sample up and down through the heating chamber and the cooling chamber; a door transporting device for slidingly moving the opening/closing door; and a central control part for controlling the flame supplying part, the electric heating part, the opening/closing door, the cooling nozzle, the sample lifting device and the door transporting device independently and respectively.

In accordance with a simulation test system of thermal impact ageing for a power transmission insulator, since the heating chamber and the cooling chamber are configured independently from each other and thus heating and cooling tests for the test sample can be performed individually or together, it is possible to realize a deterioration mechanism due to a forest fire more precisely. Therefore, it is possible to obtain a high reliability in the analysis result of deterioration by the forest fire.

Also, it is possible to perform efficient analysis of the thermal impact ageing when performing a test of accelerated deterioration by the thermal impact ageing under a test condition in which severe properties obtained from analysis of properties of an actual forest fire are condensed.

Furthermore, the simulation test system of thermal impact ageing for a power transmission insulator in accordance with the present invention can be utilized as an essential factor for establishing various measures and operating plans capable of preventing trouble of an insulator of a power transmission line by a forest fire.

DETAILED DESCRIPTION OF MAIN ELEMENTS

Figure 1:
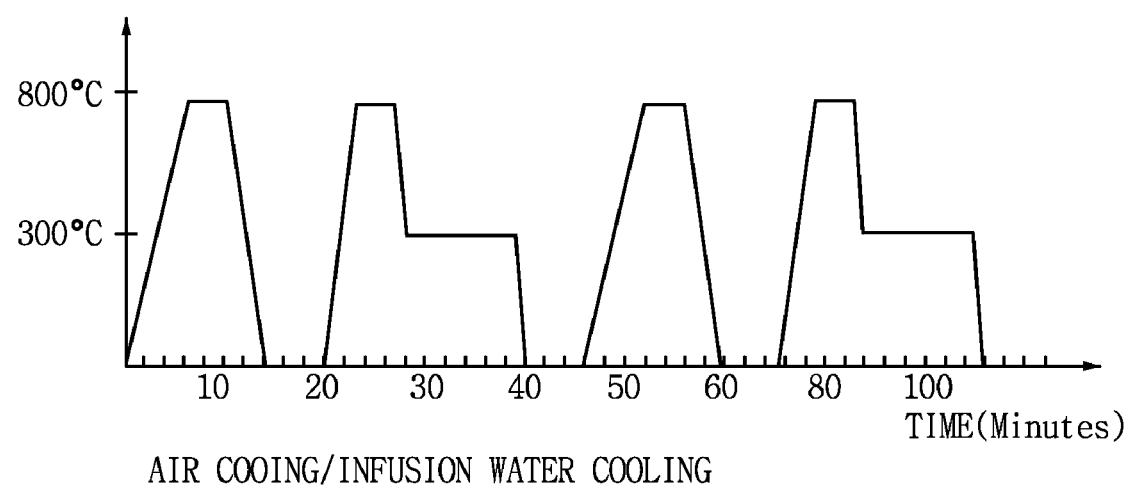
FIG. 1 shows a graph of a basic cycle of a conventional simulation test of thermal impact ageing by flame of a forest fire for a power transmission insulator.

10: fireproof wall
20: heating chamber
21: flame supplying part
22a: heating nozzle
22b: burner
23: fuel tank
24: electric heating part
25: test sample
26: support rack
27: sample transporting motor
28: ventilation port
29: ventilator
30: cooling chamber
32: cooling nozzle
34: water tank
40: partition wall
42: opening
44: opening/closing door
45: fixation rack
46: door operating motor
50: central control part

DESCRIPTION OF SPECIFIC EMBODIMENTS

The advantages, features and aspects of the invention will become apparent from the following description of the embodiments with reference to the accompanying drawings, which is set forth hereinafter.

Figure 2:
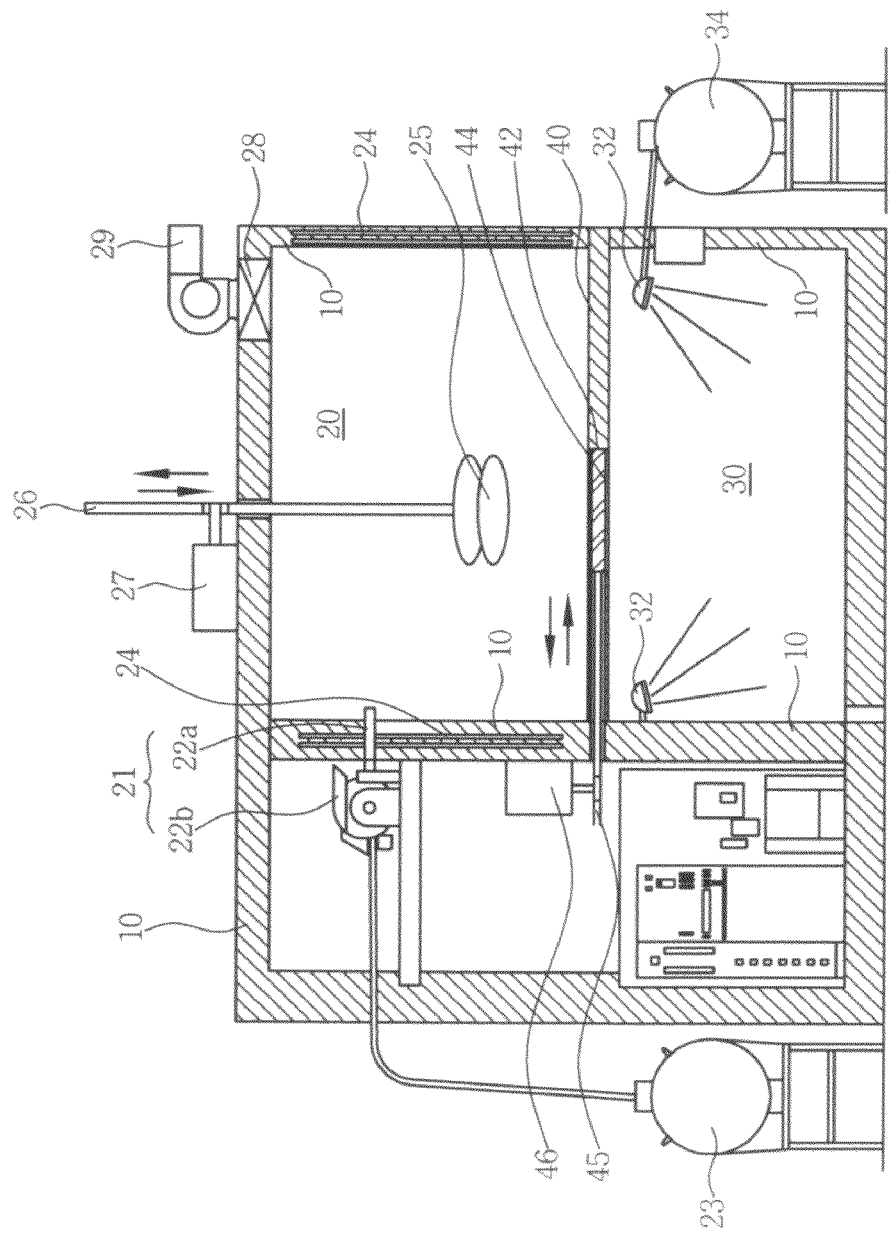
FIG. 2 shows a configuration of a simulation test system of thermal impact ageing in accordance with an embodiment of the present invention.

FIG. 1 shows a basic cycle of a simulation test of thermal impact ageing by flame of a forest fire for a power transmission insulator, and FIG. 2 shows a configuration of a simulation test system of thermal impact ageing in accordance with an embodiment of the present invention A simulation test system of thermal impact ageing in accordance with an embodiment of the present invention includes, as shown in FIG. 2, a heating chamber 20 and a cooling chamber 30 partitioned from each other with being enclosed by fireproof walls 10. Also, the simulation test system further includes a device for lifting a sample up and down, a door transporting device and a central control part 50.

One side fireproof wall 10 of the heating chamber 20 is provided with a flame supplying part 21. The flame supplying part 21 includes a heating nozzle 22a installed communicatively with an inside of the heating chamber 20 and a burner 22b to which the heating nozzle 22a is mounted. The burner 22b is supplied with fuel from a fuel tank 23. Here, the flame supplying part 21 is preferably configured so that a temperature of the flame is easily adjusted. Preferably, oil or gas is used as the fuel of the heating nozzle 22a.

Electric heating parts 24 are respectively installed in the two side fireproof walls 10 of the heating chamber 20. Here, the electric heating parts 24 are installed along a longitudinal direction of the two side fireproof walls 10 to maintain a temperature for several to tens minutes in order to confirm a flame resistance against a forest fire.

Figure 3:
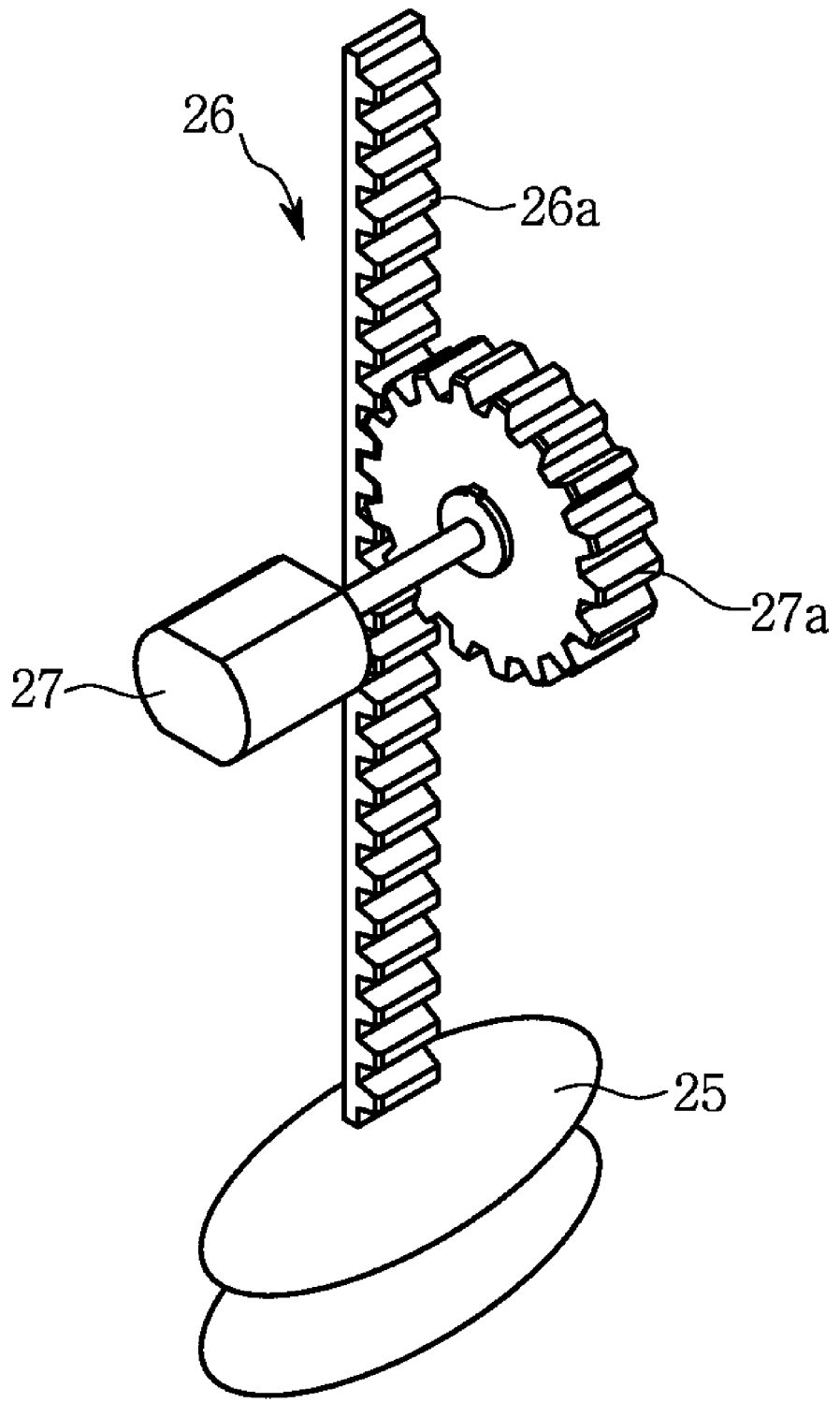
FIG. 3 shows a sample lifting device of the simulation test system in accordance with an embodiment of the present invention.

Meanwhile, in an upper part of the heating chamber 20, a test sample 25 (insulator) is lifted up and down by the sample lifting device. The sample lifting device includes, as shown in FIG. 3, a support rack 26 which supports the test sample 25 and is formed with a gear part 26a along its surface and a sample transporting motor 27 having, at its shaft, a pinion gear 27a which is engaged with the gear part 26a of the support rack 26. Here, as the sample transporting motor 27 rotates clockwise or counterclockwise, the support rack 26 is moved up and down by the gear part 26a which is engaged with the pinion gear 27a and the test sample 25 is lifted up and down in the inside of the heating chamber 20.

Meanwhile, an upper fireproof wall 10 of the heating chamber 20 is provided with a ventilation port 28 and a ventilator 29 is installed in the ventilation port 28. Here, the ventilator 29 functions to exhaust smoke generated in the heating chamber 20 by the flame supplying part 21.

Therefore, the heating chamber 20 can set a temperature of the flame similarly to an actual condition by easily adjusting the temperature of the flame with the flame supplying part 21 and, at the same time, adjusting a distance between the test sample 25 and the flame supplying part 21 through the sample lifting device. Also, the temperature of the flame can be set in a hybrid manner by supplying radiant heat simultaneously through the electric heating part 24.

The cooling chamber 30 is placed under the heating chamber 20 and is partitioned from the heating chamber 20 by a partition wall 40. And, The two side fireproof walls 10 of the cooling chamber 30 is provided with cooling nozzles 32 for spraying cooling. Here, the cooling nozzle 32 is supplied with the cooling water from a water tank 34 through a pump (not shown) to cool the test sample 25.

The partition wall 40 partitions the cooling chamber 30 and the heating chamber 20 and is provided with an opening 42 in the middle of the partition wall 40. The opening 42 of the partition wall 40 is selectively opened and closed by an opening/closing door which slides from one side of the heating chamber 30.

Figure 4:
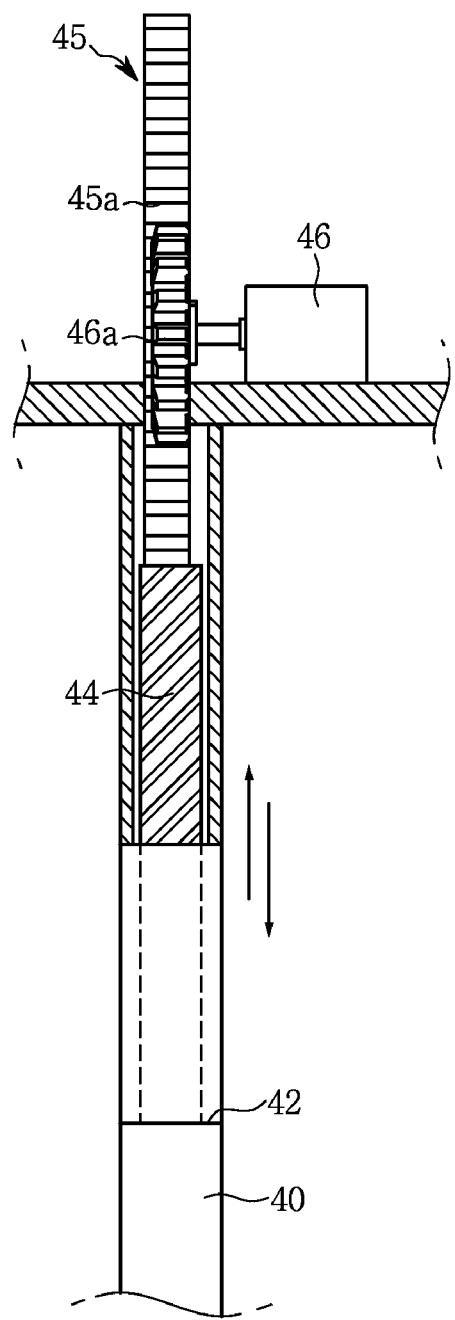
FIG. 4 shows a door transporting device of the simulation test system in accordance with an embodiment of the present invention.

The door transporting device includes, as shown in FIGS. 2 and 4, a fixation rack 45 which is fixed to one side of the opening/closing door 44 and is formed with a gear part 45a along its surface and a door operating motor 46 having, at its shaft, a pinion gear 46a which is engaged with the gear part 45a of the fixation rack 45. Here, as the door operating motor 46 rotates clockwise or counterclockwise, the fixation rack 45 is moved left and right by the gear part 45a which is engaged with the pinion gear 46a and the opening/closing door 44 selectively blocks the opening 42 of the partition wall 40.

In the cooling chamber 30, thermal impact ageing test for the test sample is implemented. That is to say, the simulation test for thermal impact ageing on the test sample 25 is implemented by spraying the cooling water through the cooling nozzles 32 when the test sample 25 is entered from the heating chamber 20 into the cooling chamber 30 by the sample lifting device in a state that the opening/closing door 44 of the partition wall 40 is opened.

The central control part 50 is disposed in one side of the cooling chamber 30 and controls the flame supplying part 21, the electric heating part 24, the opening/closing door 44, the cooling nozzle 32, the sample lifting device and the door transporting device independently and respectively.

That is to say, the central control part 50 controls a temperature of the flame supplying part 21 and a temperature of the electric heating part 24 in the heating chamber 20, controls the distance between the flame supplying part 21 and the test sample 25 through the sample lifting device and also controls amount and time of cooling water spray from the cooling nozzle 32 in the cooling chamber 30.

Of course, the central control part 50 controls operations of the sample transporting motor 27, the door operating motor 46 and the ventilator 29.

In accordance with the simulation test system for thermal impact ageing of a power transmission insulator of the present invention, since the heating chamber 20 and the cooling chamber 30 are configured independently from each other and thus heating and cooling tests for the test sample 25 can be performed individually or together, it is possible to realize a deterioration mechanism due to a forest fire more precisely and consequently obtain a high reliability in the analysis result of deterioration by the forest fire.

While the present invention has been described with respect to the specific embodiments, it will be apparent to those skilled in the art that various changes and modifications may be made without departing from the spirit and scope of the invention as defined in the following claims.

What is claimed is:

1. A simulation test system of thermal impact ageing for a power transmission insulator, comprising:
   a heating chamber provided with a flame supplying part in a side of fireproof wall and electric heating parts in two sides of the fireproof walls in a longitudinal direction of the fireproof walls;
   a sample lifting device for selectively lifting a test sample up and down in the heating chamber; and
   a central control part for controlling the flame supplying part, the electric heating part and the sample lifting device independently and respectively.

2. The simulation test system of thermal impact ageing for a power transmission insulator of claim 1, further comprising: a cooling chamber formed independently under the heating chamber.

3. The simulation test system of thermal impact ageing for a power transmission insulator of claim 2, wherein a partition wall provided with an opening is formed between the heating chamber and the cooling chamber, and an opening/closing door for selectively passing the test sample through the opening is provided in the opening of the partition wall.

4. The simulation test system of thermal impact ageing for a power transmission insulator of claim 3, wherein the cooling chamber is provided with cooling nozzles for spraying cooling water on the fireproof walls in two sides thereof to cool the test sample.

5. The simulation test system of thermal impact ageing for a power transmission insulator of claim 4, wherein the central control part controls amount and time of cooling water spray from the cooling nozzle in the cooling chamber.

6. The simulation test system of thermal impact ageing for a power transmission insulator of claim 3, wherein the opening/closing door slidingly moves with respect to one side of the partition wall by a door transporting device to open and close the opening.

7. The simulation test system of thermal impact ageing for a power transmission insulator of claim 6, wherein the door transporting device includes a fixation rack which is fixed to one side of the opening/closing door and is formed with a gear part along its surface and a door operating motor having, at its shaft, a pinion gear which is engaged with the gear part of the fixation rack.

8. The simulation test system of thermal impact ageing for a power transmission insulator of claim 1, wherein the sample lifting device includes a support rack which supports the test sample and is formed with a gear part along its surface and a sample transporting motor having, at its shaft, a pinion gear which is engaged with the gear part of the support rack.

9. The simulation test system of thermal impact ageing for a power transmission insulator of claim 1, wherein the heating chamber is provided with a ventilator for exhausting smoke generated by the flame supplying part.

10. The simulation test system of thermal impact ageing for a power transmission insulator of claim 1, wherein the central control part controls a temperature of the flame supplying part and a temperature of the electric heating part in the heating chamber and a distance between the flame supplying part and the test sample through the sample lifting device.

11. A simulation test system of thermal impact ageing for a power transmission insulator, comprising:
    a heating chamber provided with a flame supplying part and electric heating parts in fireproof walls and a partition wall having an opening/closing door in a lower part thereof;
    a cooling chamber placed under the heating chamber and provided with a cooling nozzle in a fireproof wall;
    a sample lifting device for selectively lifting a test sample up and down through the heating chamber and the cooling chamber; a door transporting device for slidingly moving the opening/closing door; and
    a central control part for controlling the flame supplying part, the electric heating part, the opening/closing door, the cooling nozzle, the sample lifting device and the door transporting device independently and respectively.

12. The simulation test system of thermal impact ageing for a power transmission insulator of claim 11, wherein the central control part controls a temperature of the flame supplying part and a temperature of the electric heating part in the heating chamber and a distance between the flame supplying part and the test sample through the sample lifting device and amount and time of cooling water spray from the cooling nozzle in the cooling chamber.

* * * * *